United States Patent [19]

Mann

[11] Patent Number: 4,977,890
[45] Date of Patent: Dec. 18, 1990

[54] HAND SPLINT

[75] Inventor: Donaerl B. Mann, St. Petersburg, Fla.

[73] Assignee: Interstate Medical Marketing, Inc., Clearwater, Fla.

[21] Appl. No.: 438,770

[22] Filed: Nov. 17, 1989

[51] Int. Cl.$^5$ ............................. A61F 5/10; A61F 5/04
[52] U.S. Cl. ..................................... 128/77; 128/87 R
[58] Field of Search ..................... 128/87 R, 89 R, 85, 128/87 A, 878, 879, 77

[56] References Cited

U.S. PATENT DOCUMENTS

| | | | |
|---|---|---|---|
| 3,788,307 | 1/1974 | Kisfner | 128/77 |
| 3,938,509 | 2/1976 | Barber | 128/89 R X |
| 4,644,938 | 2/1987 | Yates et al. | 128/77 X |
| 4,677,971 | 7/1987 | Lindemann | 128/87 R |
| 4,862,877 | 9/1989 | Barber | 128/77 |
| 4,873,968 | 10/1989 | Finnieston et al. | 128/87 R |

Primary Examiner—Robert A. Hafer
Assistant Examiner—Kerry Owens
Attorney, Agent, or Firm—Herbert W. Larson

[57] ABSTRACT

A hand splint for treatment of arthritic or paralyzed wrists employs a bendable wrist rod covered at a rear portion with hook and loop material. The wrist rod is bent upwardly at about a fifteen degree angle just forward of a front end of a forearm support member in a corrected position. The rod is bent downwardly up to forty-five degrees from normal to accomodate a contorted wrist. The support member is attached to the rear portion of the wrist rod with hook and loop material. Hook and loop material straps retain the patient's forearm within the support member. A front end of the wrist rod is imbedded ina palmar member which is replaceable depending on the need of the patient. An easily removable nut allows the palmar member to be removed from the wrist rod.

16 Claims, 3 Drawing Sheets

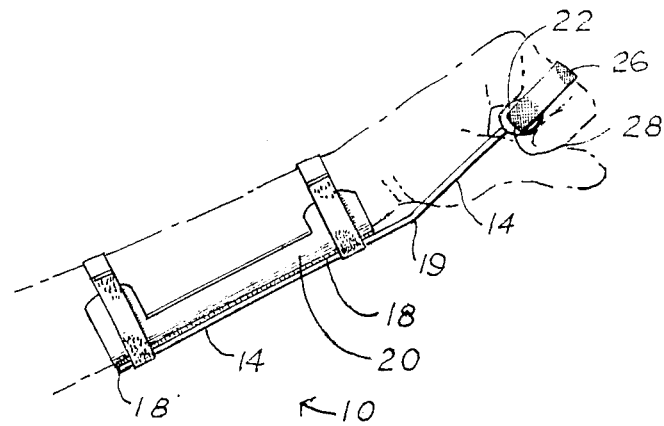
*Fig_1*
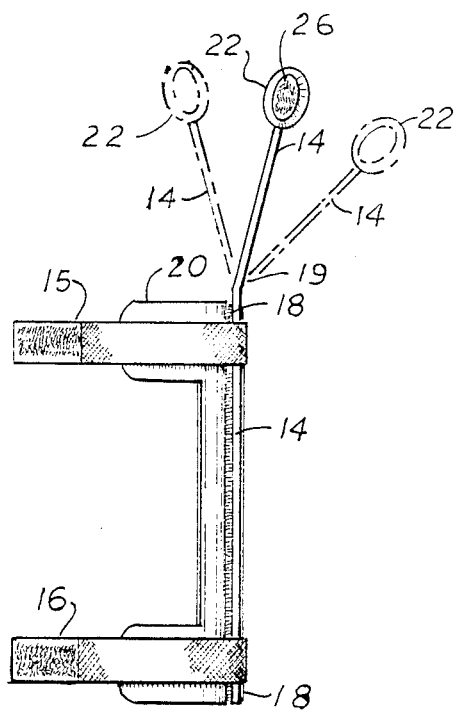
*Fig_2*
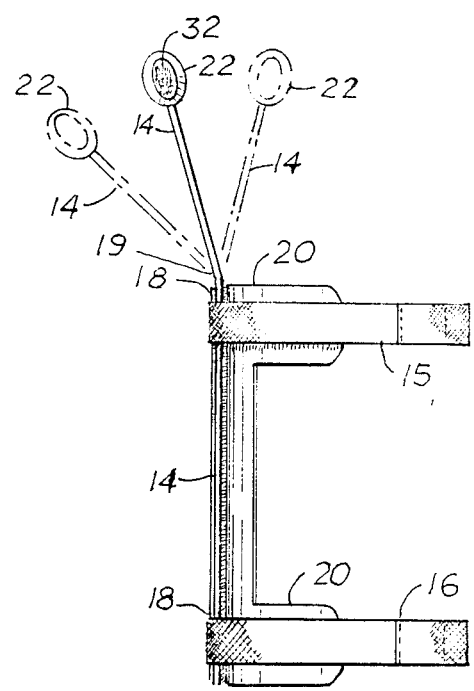
*Fig_3*

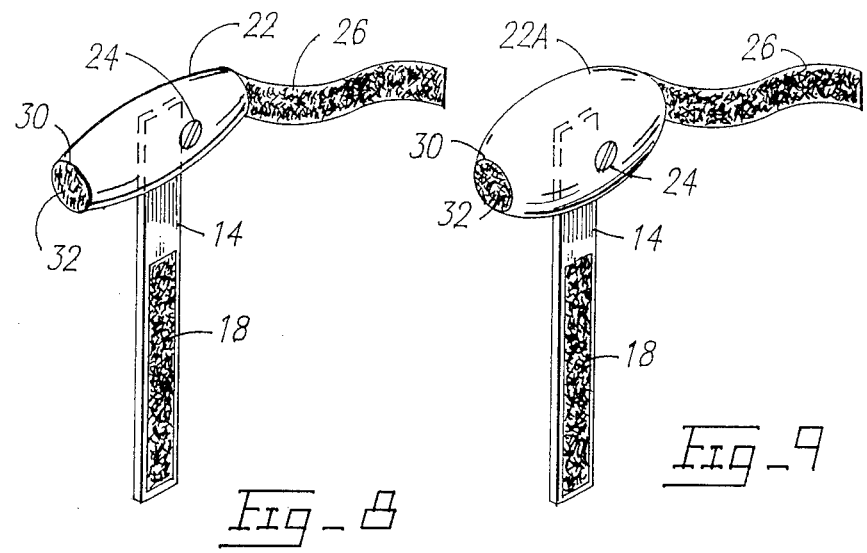

HAND SPLINT

BACKGROUND OF THE INVENTION

1. Field of the Invention.

This invention relates to hand splints. More particularly, it refers to an orthotic hand straightening device for use with stroke victims or other persons suffering from hand paralysis.

2. Description of the Prior Art.

Hand splints, such as those shown in U.S. Pat. Nos. 3,903,878 and 4,161,175, are well known and are primarily used to support a limb, particularly when one of the forearm bones is broken. In addition, other splints such as described in U.S. Pat. Nos. 3,938,509 and 4,538,600 are used to correct orthotic conditions or paralytic conditions caused by stroke. These latter corrective splints assist physical therapists in relieving the effects of a paralyzed hand which tends to turn in towards the wrist and prevents the patient from using his or her fingers. Although the splints set forth in the above indicated patents are effective for treatment of wrist paralyzed patients, a problem frequently occurs in trying to position the paralyzed wrist on the splint. The contorted position of the wrist makes such positioning extremely difficult. An improved hand splint is needed for patients with arthritic or paralyzed wrists which can be easily applied to the patient's wrist to support the hand and fingers in a non-contorted position.

SUMMARY OF THE INVENTION

I have invented an improved hand splint for use on arthritic and paralyzed patients which is easily applied to the patient's wrist and forearm and supports the hand and fingers in a more extended position. The device can be adjusted to compensate for improvement in the patient's ability to extend his or her hand.

My hand splint has a bendable wrist rod covered at a rear portion with hook or loop material and attached by such material to the bottom of a plastic forearm retaining member also covered with hook or loop material. Straps made of hook or loop material bind the forearm retaining member and wrist rod to the patient's forearm. A front portion of the wrist rod is bent either upward or downward at about a fifteen degree angle at a pivot point just forward of the forearm retaining member. The wrist rod can be bent downwardly another thirty degrees to accommodate a contorted hand. The distal end of the wrist rod is inserted into a palmar member and is held in place by a nut. A hook or loop strap is attached at one end to the palmar member and is strapped over the patient's fingers to keep the front portion of the splint in place. Differently shaped palmar members are substituted to provide for different areas of opening within the patient's hand.

BRIEF DESCRIPTION OF THE DRAWINGS

The invention may be best understood by those having ordinary skill in the art by reference to the following detailed description when considered in conjunction with the accompanying drawings in which:

FIG. 1 is a perspective view of the hand splint of this invention strapped to a forearm and correcting a contorted hand.

FIG. 2 is a right side elevation view of the hand splint with the range of bend shown in phantom.

FIG. 3 is a left side elevation view of the hand splint with the range of bend shown in phantom.

FIG. 8 is a perspective view of the wrist rod attached to the hand grip element or palmar member.

FIG. 9 is a perspective view of the wrist rod attached to an alternate hand grip element or palmar member.

FIG. 10 is a cross sectional view of the hand splint.

FIG. 11 is a perspective view of an alternate strapping arrangement for holding the hand splint to the forearm.

DETAILED DESCRIPTION OF THE INVENTION

Figure 4:
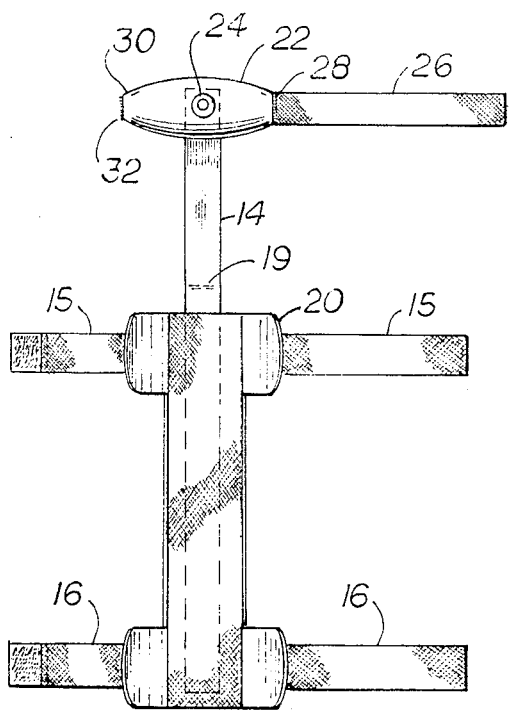
FIG. 4 is a top plan view of the hand splint.
Figure 5:
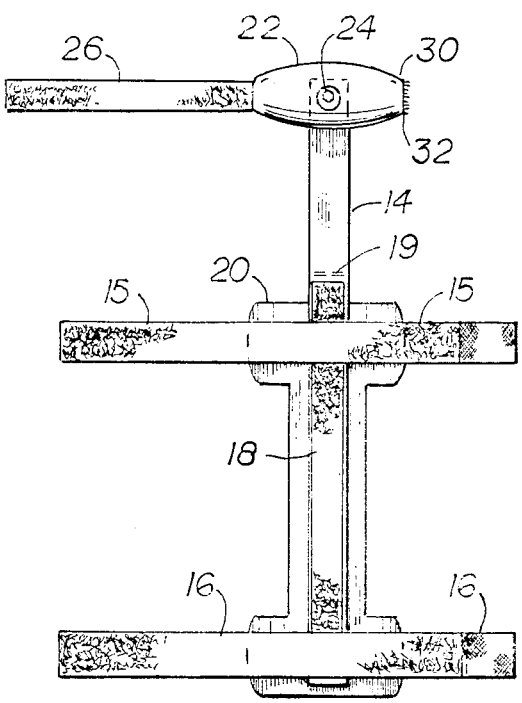
FIG. 5 is a bottom plan view of the hand splint.
Figure 6:
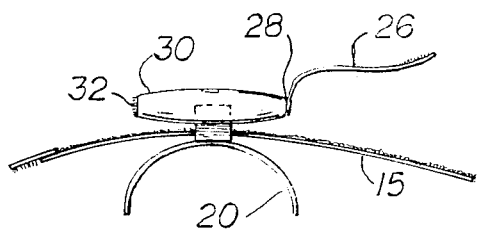
FIG. 6 is a front view of the hand splint upside down.
Figure 7:
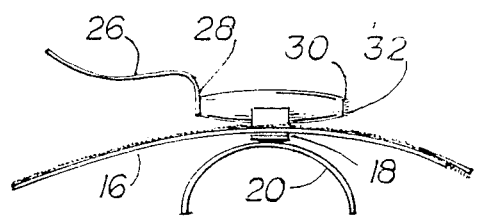
FIG. 7 is a rear view of the hand splint upside down.

Throughout the following detailed description, the same reference numerals refer to the same elements in all figures.

The hand splint 10 is attached to a forearm 12 of a patient as shown in FIG. 1. A wrist rod 14 usually made from stainless steel or heavy tensile strength aluminum and about eight inches long has a hook or loop material 18 attached by glue to a portion of each side. Hook or loop straps 15 and 16 bind the rod 14 to to a heavy duty plastic arm guard 20 and forearm 12. Hook or loop material 21 on the bottom of arm guard 20 engages corresponding hooks or loops in material 18. Arm guard 20 is made from a high strength polymer such as polyethylene or a copolymer thereof. The guard can be injection molded in one piece with U-shaped support members at each end.

Rod 14 is bent downward or upward at a fifteen degree angle from normal at a pivot point 19 just forward of arm guard 20. The desired fifteen degree bend direction is achieved by turning rod 14 with respect to the bottom surface of arm guard 20. The range of bend downward can be increased another thirty degrees to as much as forty-five degrees to allow for a severely contorted hand. The rod 14 can be bent by a medical professional to the forty-five degree angle or less as required for the patient. As the patient begins to recover, the rod 14 is bent further and further back towards the position of a fifteen degree upward bend to achieve the non-contorted position of the hand. A palmar device 22 is affixed to the end of rod 14 by a removable nut 24. The general oval or egg shape of the palmar device 22 can be varied as shown in FIG. 9. See device 22A. This variability is used to accomodate patients with varying size spaces in the palmar region. Use of too large a palmar device might hurt some patients and too small a device may prevent speedy recovery.

A hook or loop strap 26 is glued to first end 28 of the palmar device 22. A second end 30 of the palmar device 22 has a small piece of hook or loop 32 glued in place to accomodate the hook or loop 26 after it is wound around the patient's hand to bind the palmar device to the fingers.

As seen in FIG. 10 the palmar device 22 can be quickly interchanged by merely moving nut 24 and inserting a different palmar device 22A. An absorbent sock 34 can be added around the palmar device 22 or 22A to give additional comfort to the patient's hand as seen in FIG. 11. Supplementary hook and loop type straps 36 and 38 may be added to give additional support to the patient's forearm and wrist. These added straps are shown in FIG. 11.

The present invention has been illustrated by the description of the preferred embodiment in considerable detail. It is not the intention of the applicant to restrict or limit the scope of the appended claims to such detail. Additional advantages and modifications will readily appear to those skilled in the art. The invention in its broader aspects is therefore not limited to the specific details, representative apparatus and illustrative examples shown and described. Accordingly, departures may be made from such details without departing from the spirit or scope of applicant's general hand splint invention.

Having thus described the invention, what is claimed and desired to be secured by Letters patent is:

1. A device for controlling wrist and hand deformities comprising, a bendable rod having a hook or loop material fixed to at least one longitudinal surface,
   a forearm support member attached to a top surface of a rear portion of the bendable rod,
   a pair of hook or loop straps binding the bendable rod and forearm support member to the forearm of a patient,
   the bendable rod being bent at a range of fifteen degrees upwardly to forty five degrees downwardly measured from a straight line extending along the rod from a pivot point adjacent a forward portion of the forearm support member,
   a removable palmar member attached to a front portion of the bendable rod distal from the forearm support member and a hook or loop material attached at a first and second end of the palmar member so that fingers of the patient's hand are closely secured to the palmar member when the hooks or loops at one end are attached snugly to the hooks or loops at the second end.

2. The device according to claim 1 wherein the bendable rod is made from stainless steel.

3. The device according to claim 1 wherein the bendable rod is made from aluminum.

4. The device according to claim 1 wherein the hook or loop material is attached along a top and bottom longitudinal surface of the bendable rod and a bottom surface of the forearm support member has a corresponding mating hook or loop material attached to the bottom surface.

5. The device according to claim 1 wherein the forearm support member is made from a high strength polymer and has upwardly extending U-shaped forearm support arms on a front and rear portion.

6. The device according to claim 5 wherein the forearm support member is a molded polyethylene.

7. The device according to claim 5 wherein the forearm support member is a molded polyethylene copolymer.

8. The device according to claim 1 wherein the bendable rod is bent upwardly or downwardly at an angle of fifteen degrees from normal.

9. The device according to claim 1 wherein the palmar member is egg shaped in appearance.

10. The device according to claim 9 wherein the palmar member has an absorbent fabric material around its outer surface.

11. The device according to claim 1 wherein the palmar member is oval in appearance.

12. A hand splint comprising,
    a rod bent upwardly at up to fifteen degrees or downwardly at an angle of at least fifteen degrees at a pivot point,
    a forearm support member attached to a top surface of a rear portion of the rod posterior to the pivot point,
    a removable palmar member attached to the rod at an end distal from the forearm support member and
    a strap attached at a first end of the palmar member to tightly hold a patient's fingers around the palmar member by attachment of the strap to a second end of the palmar member.

13. A hand splint according to claim 12 wherein the rod is about eight inches long.

14. A hand splint according to claim 12 wherein the rod and forearm support member are held to a patient's forearm by a pair of hook or loop straps.

15. A hand splint according to claim 12 wherein the rod is made from stainless steel.

16. A hand splint according to claim 12 wherein the rod is made from aluminum.

* * * * *